United States Patent [19]

Baiocchi et al.

[11] Patent Number: 4,999,367

[45] Date of Patent: Mar. 12, 1991

[54] ETHERS OF 1-BENZYL-3-HYDROXYMETHYL-INDAZOLE WITH ALIPHATIC 2-HYDROXYACIDS, COMPOSITIONS AND USE

[75] Inventors: Leandro Baiocchi; Bruno Silvestrini, both of Rome, Italy

[73] Assignee: Aziende Chimiche Ruinite Angelini Francesco A. C. R. A. F. S. p. A., Rome, Italy

[21] Appl. No.: 470,118

[22] Filed: Jan. 24, 1990

[30] Foreign Application Priority Data

Feb. 7, 1989 [IT] Italy ............................... 47620 A/89

[51] Int. Cl.$^5$ ................... A61K 31/415; C07D 231/56
[52] U.S. Cl. ...................................... 514/403; 548/372
[58] Field of Search ......................... 548/372; 514/403

[56] References Cited

U.S. PATENT DOCUMENTS 3,470,194  9/1969  Palazzo ............................... 548/372

Primary Examiner—Robert W. Ramsuer
Attorney, Agent, or Firm—Ladas & Parry

[57] ABSTRACT

Compunds of the formula $$A-CH_2-O-CRR'-COOR''' \qquad (I)$$

wherein A, R, R' and R''' have the meanings mentioned in the description, salts thereof with pharmaceutically acceptable bases, intermediates and processes for their preparation, and analgesic pharmaceutical compositions containing them.

4 Claims, No Drawings

ETHERS OF 1-BENZYL-3-HYDROXYMETHYL-INDAZOLE WITH ALIPHATIC 2-HYDROXYACIDS, COMPOSITIONS AND USE

The present invention relates to ethers of 1-benzyl-3-hydroxymethyl-indazole with aliphatic 2-hydroxyacids, to the salts thereof with pharmaceutically acceptable bases, to intermediates and processes for their preparation, and to pharmaceutical compositions containing them.

More specifically, a first object of the present invention is to provide a compound of the formula

A—CH$_2$—O—CRR'—COOR'''     (I)

where A is a 1-benzyl-indazol-3-yl nucleus of the formula

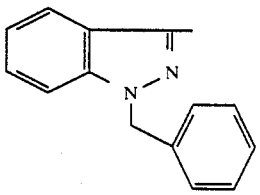

R and R' may be the same or different and are H or C$_1$-C$_5$ alkyl, R''' is H or the residue of an aliphatic saturated alcohol having from 1 to 4 carbon atoms; and, when R''' is H, the salts thereof with pharmaceutically acceptable bases.

It will be evident that when R and R' are different from each other the compound of formula I may exist either as a single enantiomer or as a racemic mixture. Therefore, the present invention intends to cover both the racemic mixtures and the single enantiomers, obtained either by separation from racemic mixtures according to conventional techniques or by stereospecific synthesis. When not differently specified, in the examples the starting compounds having an asymmetric carbon atom are used in the form of racemic mixtures.

Bendazac is a known compound of the formula

A—O—CH$_2$—COOH     (BZ)

wherein A has the already mentioned meaning, which is endowed with anti-inflammatory activity (U.S. Pat. No. 3,470,194). The continuous study of this compound during several years has shown that bendazac and its salts with pharmaceutically acceptable bases are active in the therapy of some dislipemias (U.S. Pat. No. 4,352,813), of retinitis pigmentosa (EP-B-131,317) and of cataract (U.S. Pat. No. 4,451,477); finally it has been found that bendazac and its salts can prevent opaqueness of contact lenses (EP-A-255,967).

The present invention is essentially based on the finding that addition of a methylene group (—CH$_2$—) between the 1-benzyl-indazol-3-yl nucleus (A) and the side chain (—O—CH$_2$—COOH) changes the pharmacological properties of bendazac and that, contrary to bendazac, the compounds of formula I are endowed with analgesic activity (Example 5).

A second object of the present invention is to provide a process for the preparation of a compound of the formula I, the process comprising:

(i)(a) reacting, according to conventional techniques, a compound of the formula A—CH$_2$—Y     (IIa)

wherein
A has the already mentioned meaning, and
Y is hydroxy, with an alkali metal or a suitable derivative thereof to give an alcoholate of the formula A—CH$_2$—OMe     (IIb)

wherein A has the already mentioned meaning, and Me is an atom of an alkali metal, and then reacting the compound IIb with a compound of the formula X—CRR'—COOR''     (IIIa)

wherein R and R' have the already mentioned meanings, X is a leaving group selected from the group comprising the halogens and the radicals of the formula —Z—SO$_2$—O— wherein Z is aryl or alkyl, and R'' is C$_1$-C$_5$ alkyl to give an ether of the formula A—CH$_2$—O—CRR'—COOR''     (Ia)

wherein A, R, R' and R'' have the already mentioned meanings; or (b) reacting, according to conventional techniques, a compound of the formula A—CH$_2$—X     (IIc)

wherein A and X have the already mentioned meanings, with an alcoholate of the formula MeO—CRR'—COOR''     (IIIb)

wherein R, R', R'' and Me have the already mentioneed meanings, to give an ether of formula Ia; or (c) reacting, according to conventional techniques, a compound of formula IIa with a ketone and chloroform in the presence of an alkaline hydroxide according to the following reaction scheme A—CH$_2$—Y + CHCl$_3$ + R—CO—R' ⟶
(IIa)

A—CH$_2$—O—CRR'—COOH
(I)

wherein A and Y have the already mentioned meanings, and R and R' may be the same or different and are a C$_1$-C$_5$ alkyl, (ii) hydrolizing, when desired, the ester Ia to give the corresponding acid of formula I according to conventional techniques, and (iii) preparing, when desired, (a) a salt of said acid of formula I with a pharmaceutically acceptable base or (b) an ester of said acid of formula I with a saturated aliphatic alcohol having from 1 to 4 carbon atoms, according to conventional techniques.

Steps (i)(a) and (i)(b) are encompassed within the process for preparing unsymmetrical ethers according to Williamson (J. March "Advanced Organic Chemistry" 3rd ed., page 342 to 344, reaction 0-14 and 0-16) and are preferably carried out in the presence of a suitable solvent, at a temperature of from room temperature to the boiling temperature of the reaction mixture for 15 minutes to 48 hours. Examples of suitable solvents are the aprotic solvents. Typical examples of preferred solvents are tetrahydrofuran, dimethylformamide, toluene, and their mixtures.

Alcoholates IIb and IIIb are preferably prepared with sodium metal, potassium metal or sodium hydride, in the presence of a suitable solvent at a temperature of from room temperature to the boiling temperature of the reaction mixture for 15 minutes to 48 hours. Examples of suitable solvents are the aprotic solvents. Typical examples of preferred solvents are tetrahydrofuran, dimethylformamide, toluene, and their mixtures.

Preferred meanings of X are chlorine, bromine and $Z-SO_2-O-$ wherein Z is p-methyl-phenyl, phenyl and methyl.

Step (i)(c) is preferably carried out at the boiling temperature of the reaction mixture for 30 minutes to 12 hours.

Step (ii) is preferably carried out with an alkaline aqueous or alcoholic aqueous solution at a temperature of from room temperature to the boiling temperature of the reaction mixture for 1 to 48 hours.

Typical examples of pharmaceutically acceptable inorganic bases suitable for use in step (iii)(a) are alkali and earthalkaline metals; more specifically sodium, potassium and calcium. Typical examples of organic pharmaceutically acceptable bases are primary and secondary amines optionally substituted by hydroxy and/or carboxy groups. Specific examples of said organic bases are: methylamine, isopropylamine, hexylamine, diethylamine, ethanolamine, 2-hydroxymethyl-2-amino-1,3-propanediol, glucamine, glycine, alanine, valine, leucine, isoleucine, serine, threonine, aspartic acid, glutamic acid, arginine, lysine, cystine, cysteine, methionine, phenyl alanine, tyrosine, tryptophan, and histidine.

Typical examples of preferred alcohols for use in step (iii)(b) are those having a straight chain.

A further object of the present invention is to provide an intermediate compound of the formula

  (II)

wherein A is a 1-benzyl-indazol-3-yl nucleus, and W is OH, OMe (where Me is an alkali metal atom) or a leaving group selected from the group comprising the halogens and the radicals of the formula $Z-SO_2-O-$ wherein Z is aryl or alkyl.

Preferred leaving groups are bromine, chlorine and $Z-SO_2-O-$ wherein Z is p-methyl-phenyl, phenyl or methyl.

The alcohol of formula II ($A-CH_2-OH$) may be prepared by reducing an acid of the formula

  (IV)

wherein A has the already mentioned meaning, or an aliphatic ester thereof, according to conventional techniques. Preferably, the reduction of said ester is carried out with a suitable reducing agent, such as lithium aluminium hydride, sodium bis-(2-methoxy-ethoxy) aluminium hydride (70% in toluene) or calcium tetra-(iso-propoxy)-alanate (70% in toluene) in the presence of a suitable solvent, at a temperature of from 0° C. to the boiling temperature of the reaction mixture for 30 minutes to 12 hours. Examples of suitable solvents are diethyl ether, tetrahydrofuran, toluene and their mixtures.

The corresponding alcoholates (W=OMe), halides (W=halogen), and sulfonic esters ($W=O-SO_2-Z$) may also be prepared in a easy manner according to conventional techniques.

For practical applications in therapy the compounds of this invention and their pharmaceutically acceptable salts can be administered as they are, but they are preferably administered in the form of pharmaceutical compositions.

Said compositions are another object of the present invention and contain an effective amount of one or more compouds of formula I or of their salts with pharmaceutically acceptable organic or inorganic bases, together with liquid or solid pharmaceutical excipients suitable for systemic administration as oral, peroral, rectal and parenteral administration or topical, such as aerosol or ophthalmic administration.

The pharmaceutical compositions of this invention can be in solid form as tablets, pills, capsules and slow release forms, or semi-solid such as suppositories, creams and ointments, or in liquid form as solutions, suspensions and emulsions.

In addition to the usual excipients, the compositions may contain additives suitable for pharmaceutical use as preservatives, stabilizers, emulsifiers, salts for regulating osmotic pressure, buffers, flavouring and colouring agents.

When requested by particular therapies, the compositions of this invention may comprise other compatible active ingredients whose concomitant administration is therapeutically useful.

For pratical uses in therapy the effective amount of the compound of this invention to be administered may vary over a rather broad range depending on known factors, such as the specific therapy required, the pharmaceutical composition, the administration route, and the effectiveness of the specific compound of this invention which is used. However, the optimum effective amount can readly be accomplished by simple routine procedures.

The pharmaceutical compositions can be made following the conventional techniques of the pharmaceutical chemist involving mixing, granulating and compressing when necessary, or variously mixing and dissolving the ingredients as appropriate to give the desired end product.

In general, in the case of systemic administration the daily dosage of the compound I will be preferably determined in such a way to reach a tissue level of about from $10^{-5}$ to $10^{-3}M$; this level will usally be obtained with doses of from 0.5 to 100 mg/Kg. In turn, in the case of topical administration it will preferably be used a pharmaceutical composition (collyria, creams, ointments and the like) containing from 0.1 to 5% by weight of the compound of formula I or the corresponding amount of a pharmaceutically acceptable salt thereof.

Finally, another object of this invention is to provide a method of treatment comprising administering to a patient in need thereof an effective amount of a compound of formula I or of a pharmaceutically acceptable salt thereof.

For the purpose of better illustrating the invention the following examples are now given:

EXAMPLE 1

(a) 1-benzyl-3-hydroxymethyl-indazole

Into a suspension of 2 g of lithium aluminium hydride in 50 ml of diethyl ether is dropped, under stirring, a solution of 12.5 g of the ethyl ester of the 1-benzyl-3-indazole-carboxylic acid (Von Auwers Schaich, Chem. Ber., 54, 1756, (1921)) in 30 ml of anhydrous tetrahydrofuran.

When the addition is over, the reaction mixture is refluxed for 90 minutes. After cooling, the reaction mixture is worked out in a standard manner and the resulting precipitate is filtered off and the residue obtained by evaporation of the solvent is recrystallized from isopropyl alcohol. 1-benzyl-3-hydroxymethyl-indazole is thus obtained (Compound IIa) m.p.=85°–86° C.

(b) Ether of 1-benzyl-3-hydroxymethyl-indazole with glycolic acid.

2.4 g of sodium hydride (60% suspension in oil) are added to a solution of all the amount of 1-benzyl-3-hydroxymethylindazole obtained as described above, in 70 ml of tetrahydrofuran and the reaction mixture is heated to reflux under a stream of an inert gas (nitrogen). A solution of 3.5 g of bromoacetic acid in 40 ml of tetrahydrofuran is then added and the reaction mixture is refluxed for 90 minutes. After cooling, the reaction mixture is worked out in a standard manner and acidified. The resulting product is recrystallized from isopropanol. The ether of 1-benzyl-3-hydroxymethylindazole with glycolic acid is thus obtained (Compound I, R=R'=R'''=H), m.p. 136°–138° C.

EXAMPLE 2

(a) 1-benzyl-3-chloromethyl-indazole

A solution of 11 g of 1-benzyl-3-hydroxymethyl-indazole (prepared as disclosed in example 1a) and of 11.9 g of thionyl chloride in 100 ml of toluene is refluxed for 4 hours. The solid residue which is obtained by evaporation of the solvent is consisting of crude 1-benzyl-3-chloromethyl-indazole (Compound II, W=Cl) and is used in the following step (b) without further purification. A sample recrystallized from hexane melts at 89°–91°.

(b) Ether of 1-benzyl-3-hydroxymethyl-indazole with lactic acid and ethyl ester thereof 2.7 g of sodium hydride (60% suspension in oil) are added portionwise in about 60 minutes to a solution of crude 1-benzyl-3-chloromethyl-indazole, prepared as described above, and of 53 g of ethyl lactate in 100 ml of dimethylformamide under reflux. When the addition is over, the reaction mixture is refluxed for further 30 minutes, then the reaction mixture is cooled and diluted with water; the oil which separates is extracted with ethyl acetate.

The residue obtained by evaporation of the solvent is consisting of crude ethyl ester (Compound I, R=H, R'=CH$_3$, R'''=C$_2$H$_5$) and is dissolved in a solution of 560 g of alcohol/water 1:1 containing 3.4 g of NaOH. After boiling for four hours most of the alcohol is evaporated, the remaining aqueous solution is acidified and the resulting solid is recrystallized from a mixture of hexane and ethyl acetate. The ether of 1-benzyl-3-hydroxymethyl-indazole with lactic acid is thus obtained (Compound I, R=R'''=H, R'=CH$_3$) m.p. 126°–128° C.

Alternatively, NaH is added at room temperature and when the addition is over the reaction mixture is heated to 40°–50° C.

Operating as described in example 2(b), but using methyl 2-hydroxy-butyrate, methyl 2-ethyl-2-hydroxy-butyrate and methyl 2-hydroxy-caproate instead of ethyl lactate, the compounds of formula I wherein R, R' and R''' have the meanings indicated herein below can be prepared R=H; R'=C$_2$H$_5$; R'''=CH$_3$ (ester) and H (acid),
R=C$_2$H$_5$; R'=C$_2$H$_5$; R'''=CH$_3$ (ester) and H (acid),
R=H; R'=C$_4$H$_9$; R'''=CH$_3$ (ester) and H (acid).

EXAMPLE 3

Ether of 1-benzyl-3-hydroxymethyl-indazole with 2-hydroxy2-methyl-propionic acid Into a round-bottomed flask, provided with a vigorous stirrer, 1.9 g of NaOH, 10 g of acetone and 2.38 g of 1-benzyl3-hydroxymethyl-indazole, prepared as described above, are successively added. 1.6 g of chloroform are then added (exothermic reaction) and the mixture is heated for two hours on a water bath. Water is added, the reaction mixture is washed with ethyl acetate and the aqueous solution is acidified. The residue is recrystallized from a mixture of hexane/ethyl acetate 1:1. The ether of 1-benzyl-3-hydroxymethyl-indazole with 2-hydroxy-2-methyl-propionic acid is thus obtained (Compound I, R=R'=CH$_3$, R'''=H), m.p. 132°–134° C.

EXAMPLE 4

Ether of 1-benzyl-3-hydroxymethyl-indazole with 2-hydroxy-2ethyl-propionic acid

A solution of 6 ml of chloroform and of 6.8 ml of methyl ethyl ketone is added dropwise in about 30 minutes to a suspension of 5.9 g of 1-benzyl-3-hydroxymethyl-indazole, prepared as described above, of 12 g of NaOH and of 35 ml of methyl ethyl ketone. When the addition is over, the reaction mixture is heated to reflux. After 60 minutes, the reaction mixture is cooled, water is added and the aqueous phase is separated and acidified. The resulting oil is extracted with diethyl ether and the solvent is evaporated to give an oil that hardens and is crystallized from hexane/ethyl acetate 1:1; the ether of 1-benzyl-3-hydroxymethyl-indazole with 2-hydroxy-2-ethyl-propionic acid is thus obtained (Compound I, R=CH$_3$, R'=C$_2$H$_5$, R'''=H), m.p. 115°–116° C.

Operating as described in example 4, but using 2- and 3-pentanone, 2- and 3-hexanone, 2-, 3- and 4-heptanone, 3-octanone, 5-nonanone and 6-undecanone, instead of methyl ethyl ketone, the compounds of formula I wherein R, R' and R''' have the meanings indicated hereinbelow can be prepared

| | | |
|---|---|---|
| R = CH$_3$ | R' = C$_3$H$_7$ | R''' = H |
| R = C$_2$H$_5$ | R' = C$_2$H$_5$ | R''' = H |
| R = CH$_3$ | R' = C$_4$H$_9$ | R''' = H |
| R = C$_2$H$_5$ | R' = C$_3$H$_7$ | R''' = H |
| R = CH$_3$ | R' = C$_5$H$_{11}$ | R''' = H |
| R = C$_2$H$_5$ | R' = C$_4$H$_9$ | R''' = H |
| R = C$_3$H$_7$ | R' = C$_3$H$_7$ | R''' = H |
| R = C$_2$H$_5$ | R' = C$_5$H$_{11}$ | R''' = H |
| R = C$_4$H$_9$ | R' = C$_4$H$_9$ | R''' = H |
| R = C$_5$H$_{11}$ | R' = C$_5$H$_{11}$ | R''' = H |

EXAMPLE 5

The analgesic activity of the compounds of the present invention can be evaluated by means of the hot plate test and the phenyl quinone streching assay in the mouse.

A. Hot plate

The analgesic activity is tested according the method of Woolfe and MacDonald (J. Pharmacol. Exp. Ther. 80, 300, 1944) Eddy et al. (J. Pharmacol. Exp. Ther. 98, 121, 1950) Janssen and Jagenean (J, Pharm. Pharmacol. 9 381, 1957), modified.

1. "Hot plate" equipment cat. No. 7250 by the firm Ugo Basile (Cornerio - Varese - Italy)

An aluminium plate is electrically heated through an element providing heat to the whole test surface. A temperature regulator senses the plate temperature and controls the voltage feeding in order to minimize overheating. A potentiometer enables to set a predetermined temperature within the range 45° to 62° C. (±0,2° C.).

2. Inducing discomfort

A single mouse is put on the plate heated to 55±0.2° C. In order to keep the animal on the "test area", a transparent perspex cylinder is used having a diameter of 19 cm and 13 cm high. The animal shows its discomfort by one of the following responses (Eddy et al., J. Pharmacol. Exp. Ther. 98, 121, 1950:

kicking with its hind legs (S),
dancing around the restriction cylinder (D),
turning and licking its hind paws (L),
lifting one of its hind paws and keeping it close to its body (A); this latter reaction is usually shown when the analgesic effect of the drug is waning off.
jumping and trying to get out of the restriction cylinder (J).

3. Reaction time measure

The reaction time is measured by means of an incorporated electronic timer which counts 0.1 sec increments and which is operated by a pedal switch. Timer is started at the moment in which the mouse is put onto the plate and is stopped when the animal shows one of the above described reactions. Immediately after the response, the animal is removed from the plate and the time in seconds is recorded in the box corresponding to the read time with the symbol (S; D; L; A; J) corresponding to the particular type of observed response (see point 2).

4. Reading times

Basic Readings: two readings are made at 20 and 10 minutes, respectively, before the treatment. The mean of these two readings is the "Normal Reaction Time" (Janssen e Jagenean, J. Pharm. Pharmacol., 9, 381, 1957).

Readings after the treatment: are made at 10—20—30—40—50—60—90—120 minutes after the treatment.

Extent of the reading time: the maximun extent of the observation time should not be more than 30 seconds to avoid any lesion to the animal paws. After said time, in absence of response, the animal is removed from the plate and the reaction time is reported as ">30"; the number 30 is used in the calculation (Eddy and Leimbach, J. Pharm. Exp. Ther. 107, 385, 1953).

5. Positive responses

This parameter represents an "End Point" for computing $ED_{50}$ and is defined as follows (Janssen and Jagenean J. Pharm. Pharmacol. 9, 381, 1957): a response is considered to be positive when the reaction time is at least once >30 or when at least in 3 readings the reaction time is 3 times or more greater than the normal reaction time.

6. Experimental groups and treatments Groups of two animals for each product and each dose are formed up to maximum of 14 mice. The treatments are performed mainly via intraperitoneal or subcutaneous administration.

B. Phenyl quinone stretching assay

The test is performed in the mouse according to the method of Henderson and Forsaith (J. Pharmacol. Exp. Ther. 125, 237, 1959), modified.

Algogenic agent: 0.08% (20 mg/25 ml) phenylquinone (2-phenyl1,4-benzoquinone) suspended in corn oil according to Loux, Smith and Salem (Arzneim, Forsch. 28, 1644, 1978).

Experimental groups and phenylquinone administration: experimental groups of 4 mice (20–30 g) are formed wherein each animal is marked with picric acid (saturate solution in alcohol). All animals of each group are treated i.p. with phenylquinone (10 ml/kg to each animal having a body weight higher than 25 g and ??? 0.25 ml to each animal having a body weight lower than 25 g), housed in a transparent plastic cage (23.5×13.7×13.1 cm) and observed by an experimentalist for a period of 20 minutes after the administration of phenylquinone.

Stretching counting and evaluation: the observers register the number of stretchings for each animal by means of a push-operated counter.

The stretchings are classified as follows:

full=abdomen contraction, periodical trunk torsion, and extension of the hind legs;
half=abdomen contraction and some trunk torsion. Every two stretchings the observer register a full one.

Treatments: the products are administered orally (os) or subcutaneously (sc) at −30 or −20 minutes from the phenyl quinone. Three animals of each group are treated with different products, the fourth animal is treated with the vehicle.

Effects of the compound of example 3 and reference drugs on the response of the mouse to the phenyl quinone and hot plate tests are shown in the following table.

TABLE

| Product | Dose mg/Kg | Phenyl quinone | | Hot plate | |
| --- | --- | --- | --- | --- | --- |
| | | No. of mice | % inhibition of writhings | No. of mice | % increase in latency time |
| Compound of example 3 | 25 os | 14 | 22 | — | — |
| | 50 os | 24 | 23 (1) | — | — |
| | 100 os | 24 | 38 (2) | — | — |
| | 400 os | — | — | 8 | 0 |
| Acetyl salicylic acid | 30 os | 11 | 0 | — | — |
| | 60 os | 13 | 25 (1) | — | — |
| | 120 os | 11 | 43 (2) | — | — |
| | 240 os | 13 | 56 (2) | 8 | 0 |
| Morphine | 0.5 sc | 9 | 52 (2) | 8 | 42 (1) |
| | 1 sc | 10 | 89 (2) | 8 | 94 (2) |
| Bendazac | 100 os | 11 | 5 | — | — |
| | 200 os | — | — | 8 | 0 |

Statistical significance as compared to control (Student's t test and split-plot method):
(1) p 0.05;
(2) p 0.01
— non tested

We claim:

1. A compound of the formula

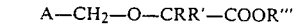

$$A-CH_2-O-CRR'-COOR''' \qquad (I)$$

where A is a 1-benzyl-indazol-3-yl nucleus, R and R' may be the same or different and are H or $C_1$-$C_5$ alkyl, R''' is H or the residue of an aliphatic saturated alcohol having from 1 to 4 carbon atoms;
and, when R''' is H, the salts thereof with pharmaceutically acceptable bases.

2. A compound of the formula I according to claim 1, wherein R and R' are methyl and R''' is hydrogen.

3. A pharmaceutical composition comprising an effective amount of a compound of the formula $$A-CH_2-O-CRR'-COOR''' \qquad (I)$$

where A is a 1-benzyl-indazol-3-yl nucleus, R and R' may be the same or different and are H or $C_1$-$C_5$ alkyl, R''' is H or the residue of an aliphatic saturated alcohol having from 1 to 4 carbon atoms;
or, when R''' is H, of a salt thereof with a pharmaceutically acceptable base, together with a pharmaceutically acceptable excipient.

4. A method of treatment comprising administering to a patient in need of an analgesic an effective amount of a compound of formula $$A-CH_2-O-CRR'-COOR''' \qquad (II)$$

where A is a 1-benzyl-indazol-3-yl nucleus, R and R' may be the same or different and are H or $C_1$-$C_5$ alkyl, R''' is H or the residue of an aliphatic saturated alcohol having from 1 to 4 carbon atoms;
or, when R''' is H, or a pharmaceutically acceptable salt thereof with a pharmaceutically acceptable base.

* * * * *